United States Patent
Cesura et al.

[11] Patent Number: 5,958,910
[45] Date of Patent: Sep. 28, 1999

[54] USE OF N-(4-ARYL-THIAZOL-2-YL)-SULFONAMIDES

[75] Inventors: Andrea Cesura, Basel, Switzerland; Stephan Röver, Inzlingen, Germany

[73] Assignee: Hoffmann-La Roche Inc., Nutley, N.J.

[21] Appl. No.: 09/197,070

[22] Filed: Nov. 20, 1998

Related U.S. Application Data

[62] Division of application No. 08/874,050, Jun. 12, 1997, Pat. No. 5,877,193.

[30] Foreign Application Priority Data

Jul. 19, 1996 [EP] European Pat. Off. ............. 96111661

[51] Int. Cl.$^6$ .................. A61K 31/425; A61K 31/44
[52] U.S. Cl. ................. 514/158; 514/342; 514/370
[58] Field of Search .................. 514/158, 342, 514/370

[56] References Cited

U.S. PATENT DOCUMENTS 5,856,347   1/1999   Hashiguchi et al. ............. 514/370

FOREIGN PATENT DOCUMENTS

| 569193 | 11/1993 | European Pat. Off. . |
| 94/27979 | 5/1994 | WIPO . |
| 96/16650 | 6/1996 | WIPO . |
| 98/33496 | 8/1998 | WIPO . |

OTHER PUBLICATIONS

Cini et al., Adv. Exp. Med. Biol., 1996, 398, 535–538.
Moroni et al., Adv. Exp. Med. Biol., 1996, 398, 203–210.
Arg. Biol. Chem. 40(b) pp. 1129–1135 (1976).
Jour. Indian Chem. Soc. vol. 39, No. 2, 1962, 121–128.
J.B. Erickson et al. Anal. Biochem. 205 pp. 257–262 (1992).
CA, vol. 97, No. 5 1982, No. 38873c.
CA, vol. 118, No. 13, 1993 No. 125015v.
CA, vol. 89, No. 25, 1978 No. 215283t.
Wiss. Zeitchrift der Univ. Halle, vol. 33, No. 3, 1984 pp. 91–93.
Antimicrobiol. Agents Chemother. vol. 40, No. 3, 1996 pp. 727–733.
Die Pharmazie, vol. 27, No. 3, 1972 p. 166.
Sci. Pharm. vol. 52, No. 1, 1984 pp. 51–58.

*Primary Examiner*—Fiona T. Powers
*Attorney, Agent, or Firm*—George W. Johnston; Patricia S. Rocha-Tramaloni; Robert A. Silverman

[57] ABSTRACT

The invention is concerned with the use of sulfonamide derivatives of the general formula

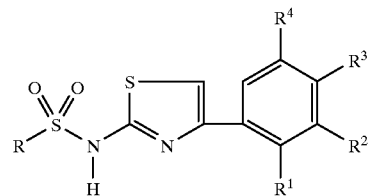

I wherein
R Signifies lower-alkyl, phenyl, benzyl, naphthyl, pyridyl or thienyl, optionally substituted by one or more lower-alkyl, lower-alkoxy, lower-alkyl carbonyl-amino, halogen, cycloalkyl, nitro, amino, methylenedioxy, phenoxy or benzyloxy substituents, and the aromatic rings, can, in turn, be substituted by nitro, halogen or amino,
$R^1$–$R^4$ signify hydrogen, halogen, hydroxy, lower-alkyl, nitro, cyano, amino, lower-alkoxy, benzyloxy, trifluoromethyl or phenyl, optionally substituted by one or more lower-alkyl, trifluoromethyl, nitro, amino or hydroxy substituents, and wherein $R^1$ and $R^2$ or $R^2$ and $R^3$ together can form a benzene ring which optionally can be substituted by halogen, trifluoromethyl, nitro, lower-alkyl or lower alkoxy,
and of their pharmaceutically acceptable salts as kynurenin-3-hydroxylase inhibitors in the control or prevention of neuro-degenerative disorders, neurological disorders resulting from an activation of the immune system, or psychiatric illnesses and, respectively, for the production of corresponding medicaments.

14 Claims, No Drawings

USE OF N-(4-ARYL-THIAZOL-2-YL)-SULFONAMIDES

This is a divisional application of U.S. Ser. No. 08/874,050, filed Jun. 12, 1997, now U.S. Pat. No. 5,877,193.

BACKGROUND OF THE INVENTION

2-Thiazolyl-sulfonamides have been known for a long time. U.S. Pat. No. 2,611,770 describes, for example, N-(2-thiazolyl)-2-hydroxypyrimidine-5-sulfonamides as active compounds against viral illnesses or illnesses caused by microorganisms.

Isoxazolyl-sulfonamides having endothelin-antoganistic activity, inter alia for the treatment of central nervous system disorders, are described in EP 569 193.

Patent Specification WO 94/27979 describes sulfonamide derivatives which contain different heterocycles and which have an endothelin-antagonistic activity.

A number of specific 2-arylsulfonamido-4-fluoroaryl-thiazoles having antifungicidal activity are set forth in Agr. Biol. Chem., 40 (6), 1129–1135, 1976.

Jour. Indian Chem. Soc., Vol. 39, No. 2, 1962 describes, inter alia, a number of specific thiazolyl-sulfonamides having pesticidal activity.

SUMMARY OF THE INVENTION

The invention is concerned with the use of sulfonamide derivatives of the formula

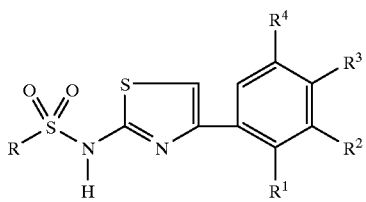

I wherein
R is lower-alkyl, phenyl, benzyl, naphthyl, pyridyl or thienyl, which are unsubstituted or substituted by one or more lower-alkyl, lower-alkoxy, lower-alkyl-carbonyl-amino, halogen, cycloalkyl, nitro, amino, methylenedioxy, phenoxy or benzyloxy substituents, and wherein the aromatic ring substituent, are unsubstituted or substituted by nitro, halogen or amino,
$R^1$–$R^4$ are, independently, hydrogen, halogen, hydroxy, lower-alkyl, lower cycloalkyl, nitro, cyano, amino, lower-alkoxy, benzyloxy, trifluoromethyl or phenyl, which are unsubstituted or substituted by one or more lower-alkyl, trifluoromethyl, nitro, amino or hydroxy substituents, and wherein $R^1$ and $R^2$ or $R^2$ and $R^3$ together can form a benzene ring which is unsubstituted or substituted by halogen, trifluoromethyl, nitro, lower-alkyl or lower-alkoxy, and of their pharmaceutically acceptable salts. The compounds of formula I and their pharmaceutically acceptable salts are useful as kynurenin-3-hydroxylase inhibitors in the control or prevention of neurodegenerative disorders, neurological disorders resulting from an activation of the immune system or psychiatric illnesses and, respectively, for the production of corresponding medicaments.

DETAILED DESCRIPTION OF THE INVENTION

In accordance with the invention it has now been found that 2-thiazolyl-sulfonamides of formula I and their salts have a surprisingly high activity as kynurenin-3-hydroxylase inhibitors. Kynurenin-3-hydroxylase inhibitors, alone or in combination with kynurenin or tryptophan, are useful for treating or preventing disorders and conditions which are associated with a malfunction of glutamatergic neurotransmission and/or which lead to an excessive production of quinolinic acid. Included among these disorders are neurodegenerative disorders (Huntington's chorea, Alzheimer's disease, Parkinson's disease, amyotrophic lateral sclerosis, epilepsy), consequences of stroke and/or cerebral ischaemia, hypoxia, multi-infarct dementia, consequences of cerebral trauma or damage as well as trauma and damage to the spinal cord, neurological disorders resulting from an activation of the immune system (e.g. AIDS-dementia complex, infections such as e.g. viral or bacterial meningitis and cancers with cerebral localization), autoimmune diseases (multiple sclerosis) as well as psychiatric illnesses (schizophrenia, chronic anxiety).

Moreover, it has been found that the compounds have antibacterial activities, for example against *Staphylococcus aureus* and *Streptococcus pyogenes*. This makes these compounds especially interesting, since a two-fold attack in one pharmaceutical application is advantageous for certain types of disease, for example in the case of bacterial meningitis or infections which are caused by the AIDS dementia complex.

Objects of the present invention are the use of compounds of formula I and of pharmaceutically usable salts thereof in the control or prevention of illnesses of the aforementioned kind and, respectively, for the production of corresponding medicaments, compounds of formulas Ia, Ib, Ic, Id and Ie and salts thereof per se and for use as therapeutically active substances, the manufacture of the compounds and salts as well as medicaments containing a compound of formulas Ia, Ib, Ic, Id or Ie or salt and the production of corresponding medicaments.

When compounds of formula I are used in the control or prevention of illnesses of the kind described above, there are preferred those compounds in which R is 4-methylphenyl, 4-methoxyphenyl, 4-aminophenyl, 3,4-dimethoxyphenyl or 2-naphthyl and $R^1$–$R^4$ signify hydrogen, fluorine, nitro or trifluoromethyl or $R^2$ and $R^3$ together form a benzene ring.

The following are examples of preferred compounds:
4-Methoxy-N-(4-naphthalen-2-yl-thiazol-2-yl)-benzene-sulfonamide,
4-amino-N-[4-(3-nitro-phenyl)-thiazol-2-yl]-benzene-sulfonamdide,
4-methyl-N-[4-(3-nitro-phenyl)-thiazol-2-yl]-benzene-sulfonamide,
3,4-dimethoxy-N-[4-(3-nitro-phenyl)thiazol-2-yl]-benzenesulfonamide,
4-methoxy-N-[4-(3-nitro-phenyl)-thiazol-2-yl]-benzenesulfonamide,
naphthalene-2-sulfonic acid [4-(3-nitro-phenyl)-thiazol-2-yl]-benzenesulfonamide,
N-[4-(2-fluoro-5-trifluoromethyl-phenyl-thiazol-2-yl]-4-methyl-benzenesulfonamide,
N-[4-(3-fluoro-5-trifluoromethyl-phenyl)-thiazol-2-yl]-4-methyl-benzenesulfonamide, 4-methyl-N-[4-(4-nitro-phenyl)-thiazol-2-yl]-benzene-sulfonamide, 4-amino-N-[4-(2-fluoro-5-trifluoromethyl-phenyl)-thiazol-2-yl]-benzenesulfonamide and 3,4-dimethoxy-N-[4-(2-fluoro-5-trifluoromethyl-phenyl)-thiazol-2-yl]-benzenesulfonamide.

The term "alkyl" used in the present description denotes straight-chain or branched saturated hydrocarbon groups such as methyl, ethyl, n-propyl, isopropyl, n-butyl, isobutyl, s-butyl, t-butyl and the like. The term "lower" denotes in this connection 1–7, preferably 1–4, carbon atoms.

The term "alkoxy" denotes an alkyl group in the sense of the foregoing definition bonded via an oxygen atom.

The term "leaving group" used in the present description embraces preferably metal-alkyl groups such as tributyltin or metal halogen groups such as for example the zinc chloride group or a boric acid group.

"Halogen" signifies fluorine, chlorine, bromine or iodine.

Compounds falling under formula I, namely compounds of formulas IA–IE, and their salts are also an object of the invention:

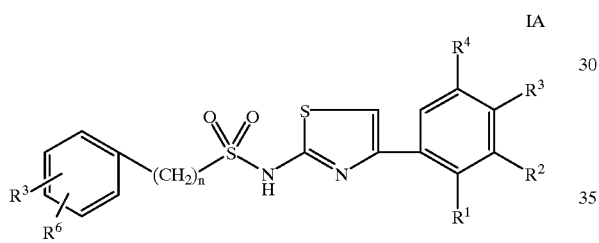

IA wherein
$R^1$–$R^4$ have the aforementioned significances,
$R^5$ is hydrogen, lower-alkyl or lower alkoxy,
$R^6$ is hydrogen, lower-alkyl, lower alkoxy, cycloalkyl, benzyl or benzyloxy and
n signifies 0 or 1 and
in which $R^5$ and $R^6$ together can form a methylenedioxy group, and with the proviso that $R^5$ and $R^6$ can not simultaneously be hydrogen;

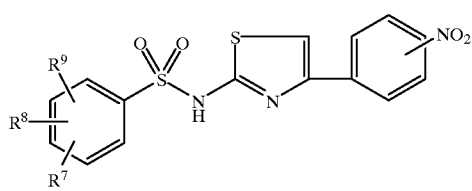

IB wherein $R^7$–$R^9$ are, independently, hydrogen, halogen, lower-alkoxy or 4-NO$_2$-phenoxy, with the proviso that at least one of $R^7$–$R^9$ is halogen;

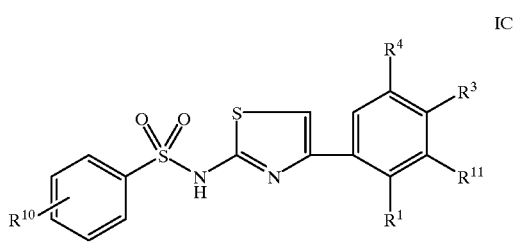

IC wherein
$R^{10}$ is amino or —NHCOR$^{12}$,
$R^{12}$ is lower alkyl,
$R^1$, $R^3$ and $R^4$ have the aforementioned significances and
$R^{11}$ is hydrogen, hydroxy, nitro, cyano, amino, trifluoromethyl, benzyloxy or phenyl, which are unsubstituted or substituted by one or more lower-alkyl, trifluoromethyl, nitro, amino or hydroxy substituents, and $R^{11}$ and $R^3$ together can form a phenyl ring;

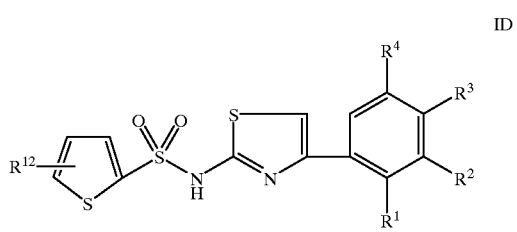

ID wherein $R^1$–$R^4$ and $R^{12}$ have the aforementioned significances;

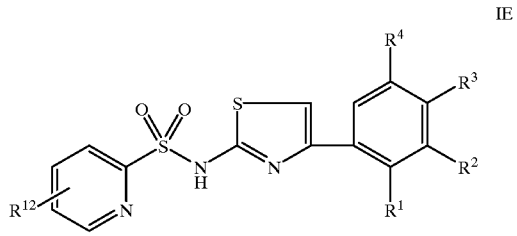

IE wherein $R^1$–$R^4$ and $R^{12}$ have the aforementioned significances.

For compounds of formula IA, there are preferred compounds in which one of $R^5$ and $R^6$ is hydrogen and one of $R^5$ and $R^6$ is lower alkyl, most preferably methyl. Also preferred are compounds in which n is 0. Also preferred are compounds of formula IA in which $R^5$ is hydrogen or lower alkoxy and $R^6$ is lower alkoxy, most preferably where $R^5$ is hydrogen or methoxy and $R^6$ is methoxy. Also preferred are compounds of formula IA in which $R^5$ and $R^6$ together from a methylenedioxy group. Also preferred are compounds of formula IA in which $R^5$ is hydrogen and $R^6$ is lower alkyl, cycloalkyl or benzyloxy. For compounds of formula IB, there are preferred compounds in which at least one of $R^7$–$R^8$ is chlorine or bromine. For compounds of formula IC, there are preferred compounds in which $R^{10}$ is —NHCOR$^{12}$ or amino. For compounds of formula ID, there are preferred compounds in which R$^{12}$ is methyl. For compounds of formula IE, there are preferred compounds in which R$^{12}$ is methyl.

The compounds of formulas Ia, Ib, IC, Id and Ie can be manufactured in accordance with the invention by a) reacting a compound of the formula

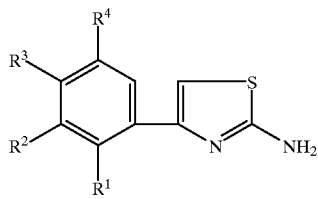

II with a suitable sulfonyl halide of the formula

III wherein R and R$^1$–R$^4$ have the aforementioned significances and X signifies halogen, or b) cleaving off the protecting group from a compound of the formula

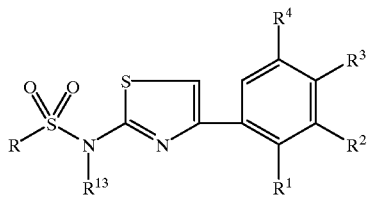

IV wherein R$^1$–R$^4$ have the significances given above and R$^{13}$ signifies a sulfonamide protecting group, or c) reacting a compound of the formula

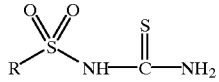

V wherein R has the significance given above, with a suitable compound of the formula

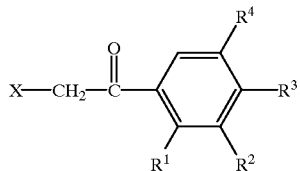

VI wherein R$^1$–R$^4$ and X have the aforementioned significances, to give a thiazole derivative of formula I, or d) reacting a suitable compound of formula IV in which R$^2$ or R$^3$ signifies bromine or iodine and R$^1$ and/or R$^4$ are/is different from bromine or iodine with a compound of the formula

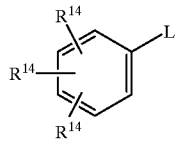

VII wherein L signifies a suitable leaving group and R$^{14}$ are the same or different and signify lower-alkyl, lower-alkoxy, trifluoromethyl, nitro, amino or hydroxy, or e) hydrolyzing a compound of formula I in which R signifies phenyl substituted by lower-alkyl-carbonyl-amino and R$^1$–R$^4$ have the aforementioned significances to a compound of formula I in which R signifies phenyl substituted by amino, and f) if desired, converting a compound of formula I into a pharmaceutically acceptable salt.

In accordance with process variant a) a compound of formula II is treated with a corresponding sulfonyl halide of formula III and stirred for several hours in the presence of pyridine.

The following are especially well suited as sulfonyl halides: p-toluenesulfonyl chloride, p-methoxybenzenesulfonyl chloride, p-Cl-benzenesulfonyl chloride, 3,4-dichlorobenzenesulfonyl chloride, benzo[1,3]dioxol-5-sulfonyl chloride, 5-isopropyl-pyridine-2-sulfonyl chloride, 3,5-dichloro-4-nitro-phenoxy-benzoyl chloride, naphthalene-2-sulfonyl chloride, 4-cyclohexyl-benzenesulfonyl chloride, 4-isopropyl-benzene-sulfonyl chloride, 4-acetamino-benzenesulfonyl chloride, 3,4-dimethoxy-benzenesulfonyl chloride, 5-tert.-butyl-thiophene-2-sulfonyl chloride, butanesulfonyl chloride and the like.

In accordance with process variant b) a compound of formula IV is deprotected. Suitable protecting groups and methods for their cleavage will be familiar to any person skilled in the art, with, of course, preferred protecting groups being those which can be cleaved off by methods involving conditions under which other structural elements in the compounds of formula IV are not affected. All known sulfonamide protecting groups are suitable as the sulfonamide protecting group, with the methoxymethylene group (MOM) being preferred. The cleavage is effected in the acidic range, for example by the addition of hydrochloric acid.

Process variant c), in which a compound of formula V and a compound of formula VI react together to form the thiazole ring, represents a further possibility for the manufacture of compounds of formula I. Conveniently, an appropriately substituted sulfonylthiourea compound dissolved in an alcohol, for example ethanol, is treated with an appropriate 2-halo-1-phenyl-1-ethanone compound and the reaction mixture is boiled for a brief period.

According to process variant d) a compound of formula IV is reacted with a compound of formula VII. Conveniently, this reaction is effected in the presence of a catalyst, for example tetrakis(triphenylphosphine)-palladium and lithium chloride with an aryl metal compound, for example phenylboric acid, in the presence of potassium carbonate. Toluene is conveniently used as the solvent. There are obtained compounds of formula I in which $R^2$ is phenyl unsubstituted or substituted by one or more lower-alkyl, lower-alkoxy, trifluoromethyl, nitro, amino or hydroxy substituents.

The salt formation in accordance with variant f) of the process in accordance with the invention is effected according to methods which are generally usual and which will be familiar to any person skilled in the art. Basic compounds of formula I can be converted into pharmaceutically acceptable acid addition salts, for example with hydrogen chloride, hydrogen bromide, phosphoric acid, sulphuric acid, citric acid, p-toluenesulfonic acid and the like. Acidic compounds of formula I can form pharmaceutically acceptable salts with suitable bases, for example alkali metal salts such as sodium or potassium salts or alkaline earth metal salts such as magnesium or calcium salts.

The starting materials of formulae II, III, IV, V, VI and VII required for the manufacture of the compounds of formula I are known compounds or can be prepared in analogy to known processes. These reactions will be familiar to any person skilled in the art. Furthermore, the preparation of some intermediates is described in Examples 52–65.

Scheme 1 hereinafter shows the preparation of compounds of formula Scheme II.

Scheme 1

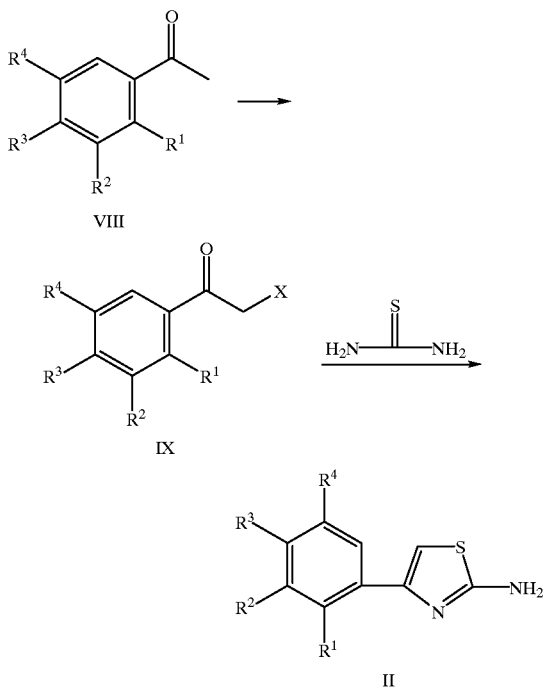

In this scheme, $R^1$–$R^4$ have the aforementioned significances and X signifies halogen.

As mentioned earlier, the sulfonamide derivatives of formula I have valuable pharmacological properties and they are accordingly useful for the control or prevention of illnesses or conditions which are associated with a malfunction of glutamatergic neurotransmission and/or which lead to an excessive production of quinolinic acid.

Kynurenic acid and quinolinic acid, two body-specific substances of the tryptophan degradation pathway via kynurenin, influence the N-methyl-D-aspartate (NMDA) binding sites of the glutamate receptor. Changes in the tissue level of these two substances are associated with neurological disorders and psychiatric illnesses. Quinolinic acid is strongly neurotoxic, while kynurenic acid exhibits neuroprotective activities. The enzyme kynurenin-3-monooxygenase (kynurenin-3-hydroxylase) is responsible in the tryptophan degradation pathway for the conversion of kynurenin into 3-hydroxykynurenin, a quinolinic acid precursor. Inhibitors of this enzyme on the one hand reduce the formation of the neurotoxin quinolinic acid and on the other hand lead to an increased formation of the neuroprotective-acting kynurenic acid by the inhibition-mediated increased availability of kynurenin.

The compounds in accordance with the invention have as kynurenin-3-hydroxylase inhibitors a higher activity than known inhibitors such as m-nitrobenzoylalanine, 3,4-dichlorobenzoylalanine and/or nicotinylalanine. The compounds in accordance with the invention are active in rodents not only after intraperitoneal injection, but also after oral administration.

Determination of kynurenin-3-hydroxylase in vitro and ex vivo

The kynurenin-3-hydroxylase inhibiting activity of the compounds in accordance with the invention can be determined in vitro and ex vivo using standard methods. The preparations to be tested were examined in the tests described hereinafter, which are based on the methods published by J. B. Erickson, E. M. Flanagan, S. Russo and J. F. Reinhard [*Anal. Biochem.* 1992, 205: 257–262].

in vitro: The enzyme source is a crude rat kidney mitochondrial preparation which, taken up in the ratio 1:70 (weight/volume) in a potassium phosphate buffer of pH 7.4, containing EGTA, is kept in the frozen state at –80° C. until used. The enzyme test for the in vitro determination differs from the ex vivo determination described hereinafter by the use of the mentioned mitochondreal preparation in place of tissue homogenates as the enzyme source and by a pre-incubation of the enzyme with the substances to be tested at 37° C. for 15 min.

ex vivo: The substances to be tested are administered orally to male rats of 100–140 g body weight in a dosage of 30 μmol/kg. The kidneys and a part of the liver are removed from the animals, which are decapitated after 2 hours, and frozen at –80° C. until used. In order to measure the enzyme activity, the organs are homogenized in the ratio 1:10 (weight/volume) in sucrose, containing TRIS/HCl, pH 7.4 and PMSF.

Measurement of the Enzyme Activity

Scheme of a typical procedure carried out in an incubation tube of appropriate size or on a microtitre plate:

25 μl of the substance to be tested in a suitable concentration (in vitro) or homogenization buffer (ex vivo)

25 μl of potassium phosphate buffer 0.2M containing 0.4 units of glucose-6-phosphate dehydrogenase 25 μl of the mitochondrial preparation (in vitro) or of the kidney or liver homogenate (ex vivo)

pre-incubation: 15 min at 37° C. (only in vitro)

25 μl of the substrate L-kynurenin containing L-$^3$H-3-kynurenin (0.1 μCi)

100 μmol, magnesium chloride 4 mmol, NADPH 200 μmol, glucose-6-phosphate 3 mmol (concentration data as final concentrations)

incubation: 10 min (in vitro) or 2 min (ex vivo) at 37° C. on a shaking machine

150 μl of a 10% suspension of active charcoal (Norit A) in water (to remove unreacted labelled substrate)

shaking for about one minute centrifugation for 4 min at 4000 revolutions/min transfer of 50 μl of the charcoal-free supernatant into a counting vessel addition of 150 μl of an appropriate scintillator to count the radioactivity of the now-tritiated water, which is a measurement of the enzyme activity which exists.

The $IC_{50}$ value is a measurement of the strength of the in vitro enzyme inhibition which is brought about by the tested substances. It is the concentration of test substance which brings about a 50% inhibition of the enzyme activity.

The $ED_{50}$ value or, where this is not achieved, the percentage inhibition after administration of a single dosage, is a measurement of the strength of the ex vivo enzyme inhibition which is brought about by the tested substances. The $ED_{50}$ value is that dosage of test substance which leads to a 50% enzyme inhibition in the investigated tissue homogenates.

| Example No. Compound | % of control at 1 μM | $IC_{50}$ [μM] | % of control 30 μM/kg p.o in the liver | $ED_{50}$ μMol/kg p.o. in the liver |
|---|---|---|---|---|
| 3 A |  | 0.04 | 43.00 |  |
| 6 B | 4.58 | 0.065 | 54.00 |  |
| 8 C | 5.00 | 0.044 | 23.00 | 9.0 |
| D | 4.00 | 0.03 | 20.00 |  |
| 21 E | 2.00 | 0.026 | 10.00 | 4.7 |
| 32 F | 2.50 | 0.043 |  | 17.0 |
| 41 G | 18.00 | 0.050 |  | 17.0 |
| 42 H | 1.40 | 0.015 |  | 4.6 |
| 46 I | 4.70 | 0.022 |  | 5.3 |

A 4-Methyl-N-[4-(3-nitro-phenyl)-thiazol-2-yl]-benzene-sulfonamide
B N-[4-(3,4-Dimethoxy-phenyl)-thiazol-2-yl]-4-methyl-benzensulfonamide
C 4-Methoxy-N-[4-(3-nitro-phenyl)-thiazol-2-yl]-benzene-sulfonamide
D Naphthalene-2-sulfonic acid [4-(3-nitro-phenyl)-thiazol-2-yl)-amide
E 3,4-Dimethoxy-N-[4-(3-nitro-phenyl)-thiazol-2-yl]-benzenesulfonamide
F N-[4-(2-Fluoro-5-trifluoromethyl-phenyl)-thiazol-2-yl]-4-methyl-benzenesulfonamide
G N-[4-(2-Fluoro-5-trifluoromethyl-phenyl)-thiazol-2-yl]-4-methoxy-benzenesulfonamide
H 4-Amino-N-[4-(2-fluoro-5-trifluoromethyl-phenyl)-thiazol-2-yl]-benzenesulfonamide
I 3,4-Dimethoxy-N-[4-(2-fluoro-5-trifluoromethyl-phenyl)-thiazol-2-yl]benzenesulfonamide As mentioned above, compounds of formula I and their salts also have an antibacterial activity, for example against *Staphylococcus aureus* and *Streptococcus pyogenes*.

The following Table shows that the antibacterial activity of compounds of formula I is comparable with that of the known antibacterial compound sulfamethoxazole (SMZ). Moreover, comparison was made with trimethoprim (TMP).

| Type | Strain | BCB | TMP | SMZ | Example 42 | Example 46 |
|---|---|---|---|---|---|---|
| *Staphylococcus aureus* | ATCC 25923 | 1003/04 | 0.5 | 32 | 16 | 32 |
| *Enterococcus faecalis* | ATCC 29212 | 1003/28 | 0.1254 | >256 | >256 | >256 |
| *Streptococcus pneumoniae* | ATCC 49619 |  | 2 | >256 | >256 | >256 |
| *Streptococcus pyogenes* | B15 | 1003/35 | 0.25 | 16 | 16 | 64 |
| *Listeria monocytogenes* | BK23 | 1003/55 | 1 | >256 | >256 | >256 |
| *Escherichia coli* | ATCC25922 | 1001/04 | 8 | 128 | 256 | >256 |
| *Pseudomonas aeruginosa* | BA | 1004/01 |  | >256 | >256 | >256 |

Method for the Determination of Antibacterial Activity

The minimum inhibitory concentration (MIC in μg/ml) was determined by the microdilution method in which an Isosensotest bouillon (Oxoid) was used and was complemented with 3% horse blood for Streptococcus and Listeria. The inoculation amount was approximately $5 \times 10^5$ CFU/ml. After incubation at 37° C. for 18 h the plates were evaluated at 650 nm. The MIC was determined as the lowest concentration of active substance which brought about a growth inhibition of ≧80% compared to the control.

The compounds of formula I and pharmaceutically acceptable salts thereof can be used as medicaments, for example in the form of pharmaceutical preparations. The pharmaceutical preparations can be administered orally, for example in the form of tablets, coated tablets, dragees, hard and soft gelatine capsules, solutions, emulsions or suspensions. The administration can, however, also be effected rectally, for example in the form of suppositories, or parenterally, for example in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble salts of compounds of formula I, but are usually not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a novel compound of formula I or a pharmaceutically acceptable salt thereof and a therapeutically inert excipient are also an object of the present invention, furthermore also a process for the production of such medicaments which comprises bringing one or more novel compounds of formula I or pharmaceutically acceptable salts thereof and, if desired, one or more other therapeutically valuable substances into a galenical administration form together with one or more therapeutically inert carriers. The dosage can vary within wide limits and will, of course, be fitted to the individual requirements in each particular case. In general, in the case of intravenous administration a daily dosage of about 1 mg to 1000 mg should be appropriate.

The object of the invention in its broadest aspect is, as mentioned earlier, the use of compounds of formula I and of pharmaceutically usable salts thereof in the control or prevention of neurodegenerative diseases, neurological disorders resulting from an activation of the immune system or psychiatric illnesses and, respectively, for the production of corresponding medicaments.

The following Examples illustrate the present invention in more detail, but are not intended to limit its scope in any manner.

EXAMPLE 1

N-[4-(4-Hydroxy-3-methyl-phenyl)-thiazol-2-yl]-4-methyl-benzenesulfonamide

A solution of 26 g of 4-toluenesulfonyl-thiourea in 225 ml of ethanol was treated with 25.9 g of 2-bromo-1-(4-hydroxy-3-methyl-phenyl)-ethanone, left to stand at room temperature for 3 days and then boiled for a brief period. The reaction mixture was evaporated to dryness in a vacuum and subsequently partitioned between water and ethyl acetate. The aqueous phase was extracted once with ethyl acetate, the organic phases were combined, dried with sodium sulphate and concentrated. The residue was chromatographed on 500 g of Kieselgel 60 with ethyl acetate/hexane (1:1) as the eluent. The product-containing fractions were concentrated and, after recrystallization from 50% ethanol, yielded 10.1 g of N-[4-(4-hydroxy-3-methyl-phenyl)-thiazol-2-yl]-4-methyl-benzenesulfonamide as colourless crystals.

M.p.: 168–170° C. (dec).

EXAMPLE 2

N-[4-(3-cyano-phenyl)-thiazol-2-yl]-4-methyl-benzenesulfonamide

A mixture of 0.5 g of 3-(2-amino-thiazol-4-yl)-benzonitrile with 0.52 g of p-toluenesulfonyl chloride was stirred overnight with 2 ml of pyridine. The resulting, red colored suspension was poured into 50 ml of 1N hydrochloric acid and the solid which thereby separated was filtered off and dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 80 ml of 50% ethanol yielded 0.35 g of N-[4-(3-cyano-phenyl)-thiazol-2-yl]-4-methyl-benzenesulfonamide as colorless crystals.

M.p.: >250° C.

EXAMPLE 3

4-Methyl-N-[4-(3-nitro-phenyl)-thiazol-2-yl]-benzenesulfonamide

A mixture of 0.5 g of 4-(3-nitro-phenyl)-thiazol-2-ylamine hydrochloride with 0.42 g of p-toluenesulfonyl chloride was stirred overnight with 2 ml of pyridine. The resulting, red colored suspension was poured into 50 ml of 1N hydrochloric acid and the solid which thereby separated was filtered off and dissolved in a mixture of 10 ml of ethanol and 10 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 40 ml of 50% ethanol yielded 0.35 g of 4-methyl-N-[4-(3-nitro-phenyl)-thiazol-2-yl]-benzenesulfonamide as yellowish crystals.

M.p.: 187–189° C.

EXAMPLE 4

N-[4-(4-Benzyloxy-3-methoxy-phenyl)-thiazol-2-yl)-benzenesulfonamide

A mixture of 0.5 g of 4-(4-benzyloxy-3-methoxy-phenyl)-thiazol-2-ylamine hydrobromide with 0.27 g of p-toluenesulfonyl chloride was stirred overnight with 2 ml of pyridine. The resulting, red colored solution was poured into 50 ml of 1N hydrochloric acid and extracted three times with 50 ml of methylene chloride each time. The organic extracts were combined, dried with magnesium sulphate and concentrated. The residue was chromatographed on 40 g of Kieselgel 60 with diethyl ether/hexane (2:1) as the eluent. Concentration of the product-containing fractions yielded 0.35 g of N-[4-(4-benzyloxy-3-methoxy-phenyl)-thiazol-2-yl]-benzenesulfonamide as colorless crystals.

M.p.: 152–155° C.

EXAMPLE 5

N-[4-(3,4-Bis-benzyloxy-phenyl)-thiazol-2-yl]-4-methyl-benzenesulfonamide

A mixture of 0.5 g of 4-(3,4-bis-benzyloxy-phenyl)-thiazol-2-ylamine hydrobromide with 0.23 g of p-toluenesulfonyl chloride was stirred overnight with 2 ml of pyridine. The resulting, red colored solution was poured into 50 ml of 1N hydrochloric acid and extracted three times with 50 ml of methylene chloride each time. The organic extracts were combined, dried with magnesium sulphate and concentrated. The residue was dissolved in a mixture of 20 ml of ethanol and 15 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 50 ml of 60% ethanol yielded 0.33 g of N-[4-(3,4-bis-benzyloxy-phenyl)-thiazol-2-yl]-4-methyl-benzenesulfonamide as colorless crystals.

M.p.: 158–161° C.

EXAMPLE 6
N-[4-(3,4-Dimethoxy-phenyl)-thiazol-2-yl]-4-methyl-benzenesulfonamide A mixture of 0.5 g of 4-(3,4-dimethoxy-phenyl)-thiazol-2-ylamine hydrobromide with 0.33 g of p-toluenesulfonyl chloride was stirred overnight with 2 ml of pyridine. The resulting, red colored solution was poured into 50 ml of 1N hydrochloric acid and extracted three times with 50 ml of methylene chloride each time. The organic extracts were combined, dried with magnesium sulphate and concentrated. The residue was chromatographed on 35 g of Kieselgel 60 with diethyl ether as the eluent. The product-containing fractions were concentrated, dissolved in 40 ml of 50% ethanol by the addition of a small amount of 2N sodium hydroxide solution and precipitated with 2N hydrochloric acid at pH 6. 0.4 g of N-[4-(3,4-dimethoxy-phenyl)-thiazol-2-yl]-4-methyl-benzenesulfonamide was obtained as colorless crystals.
M.p.: 85–87° C. (dec.)

EXAMPLE 7
N-[4-(4-Methoxy-3-methyl-phenyl)-thiazol-2-yl]-4-methyl-benzenesulfonamide A mixture of 0.5 g of 4-(4-methoxy-3-methyl-phenyl)-thiazol-2-ylamine hydrobromide with 0.5 g of p-toluenesulfonyl chloride was stirred overnight with 2 ml of pyridine. The resulting, red colored solution was poured into 50 ml of 1N hydrochloric acid and the solid which thereby separated was filtered off and dissolved in a hot mixture of 20 ml of ethanol and 50 ml of water. 0.06 g of N-[4-(4-methoxy-3-methyl-phenyl)-thiazol-2-yl]-4-methyl-benzenesulfonamide separated as beige crystals upon cooling.
M.p.: 94–96° C.

EXAMPLE 8
4-Methoxy-N-[4-(3-nitro-phenyl)-thiazol-2-yl]-benzenesulfonamide

A mixture of 0.5 g of 4-(3-nitro-phenyl)-thiazol-2-ylamine hydrochloride with 0.44 g of 4-methoxybenzenesulfonyl chloride was stirred overnight with 2 ml of pyridine. The resulting, red colored suspension was poured into 50 ml of 1N hydrochloric acid and the solid which thereby separated was filtered off and dissolved in a mixture of 40 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 40 ml of 50% ethanol yielded 0.31 g of 4-methoxy-N-[4-(3-nitro-phenyl)-thiazol-2-yl]-benzenesulfonamide as yellowish crystals.
M.p.: 157–159° C.

EXAMPLE 9
4-Chloro-N-[4-(3-nitro-phenyl)-thiazol-2-yl]-benzenesulfonamide

A mixture of 0.5 g of 4-(3-nitro-phenyl)-thiazol-2-ylamine hydrochloride with 0.45 g of 4-chlorobenzenesulfonyl chloride was stirred overnight with 2 ml of pyridine. The resulting, red colored suspension was poured into 50 ml of 1N hydrochloric acid and the solid which thereby separated was filtered off and dissolved in a mixture of 40 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 40 ml of 50% ethanol yielded 0.43 g of 4-chloro-N-[4-(3-nitro-phenyl)-thiazol-2-yl]-benzenesulfonamide as colorless crystals.
M.p.: 195–197° C.

EXAMPLE 10
3,4-Dichloro-N-[4-(3-nitro-phenyl)-thiazol-2-yl]-benzenesulfonamide A mixture of 0.5 g of 4-(3-nitro-phenyl)-thiazol-2-ylamine hydrochloride with 0.52 g of 3,4-dichlorobenzenesulfonyl chloride was stirred overnight with 2 ml of pyridine. The resulting, red colored suspension was poured into 25 ml of 1N hydrochloric acid and the solid which thereby separated was filtered off and dissolved in a mixture of 30 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 80 ml of 50% ethanol yielded 0.39 g of 3,4-dichloro-N-[4-(3-nitro-phenyl)-thiazol-2-yl]-benzenesulfonamide as yellowish crystals.
M.p.: 189–191° C.

EXAMPLE 11
Benzo[1,3]dioxol-5-sulfonic acid [4-(3-nitro-phenyl)-thiazol-2-yl]-amide A mixture of 0.5 g 4-(3-nitro-phenyl)-thiazol-2-ylamine hydrochloride with 0.52 g of benzo[1,3]dioxol-5-sulfonyl chloride was stirred overnight with 2 ml of pyridine. The resulting, red colored suspension was poured into 25 ml of 1N hydrochloric acid and the solid which thereby separated was filtered off and dissolved in a mixture of 30 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 100 ml of 60% ethanol yielded 0.30 g of benzo[1,3]dioxol-5-sulfonic acid [4-(3-nitro-phenyl)-thiazol-2-yl]-amide as yellowish crystals.
M.p.: 221–224° C.

EXAMPLE 12
5-Isopropyl-pyridine-2-sulfonic acid [4-(3-nitro-phenyl)-thiazol-2-yl]-amide A mixture of 0.5 g of 4-(3-nitro-phenyl)-thiazol-2-ylamine hydrochloride with 0.46 g of 5-isopropyl-pyridine-2-sulfonyl chloride was stirred overnight with 2 ml of pyridine. The resulting, red colored suspension was poured into 25 ml of 1N hydrochloric acid and the solid which thereby separated was filtered off and dissolved in a mixture of 30 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 40 ml of ethanol and 20 ml of ethyl acetate yielded 0.31 g of 5-isopropyl-pyridine-2-sulfonic acid [4-(3-nitro-phenyl)-thiazol-2-yl]-amide as yellowish crystals.

M.p.: 208–210° C.

EXAMPLE 13
3,5-Dichloro-4-(4-nitro-phenoxy)-N-[4-(3-nitro-phenyl)-thiazol-2-yl]-benzenesulfonamide A mixture of 0.26 g of 4-(3-nitro-phenyl)-thiazol-2-ylamine hydrochloride with 0.42 g of 3,5-dichloro-4-nitrophenoxybenzenesulfonyl chloride was stirred overnight with 2 ml of pyridine. The resulting, red coloured suspension was poured into 50 ml of 1N hydrochloric acid and the solid which thereby separated was filtered off and dissolved in a mixture of 50 ml of ethanol and 20 ml of 2N sodium hydroxide solution. After the addition of 0.5 g of active charcoal the mixture was stirred at room temperture for 30 minutes and subsequently the active charcoal was filtered off. The product separated upon neutralization with concentrated hydrochloric acid. Recrystallization from 50 ml of ethanol and 20 ml of ethyl acetate yielded 0.11 g of 3,5-dichloro-4-(4-nitro-phenoxy)-N-[4-(3-nitro-phenyl)-thiazol-2-yl]-benzenesulfonamide as yellowish crystals.

M.p.: >250° C.

EXAMPLE 14
N-[4-(4-Chloro-phenyl)-thiazol-2-yl]-4-methyl-benzenesulfonamide

A mixture of 0.3 g of 4-(4-chlorophenyl)-thiazol-2-ylamine hydrobromide with 0.22 g of p-toluenesulfonyl chloride was stirred overnight with 2 ml of pyridine. The resulting, red colored suspension was poured into 30 ml of 1N hydrochloric acid and the solid which thereby separated was filtered off and dissolved in a hot mixture of 20 ml of ethanol and 30 ml of water. 0.05 g of N-[4-(4-chlorophenyl)-thiazol-2-yl]-4-methyl-benzenesulfonamide separated as colorless crystals upon cooling.

M.p.: 237–239° C.

EXAMPLE 15
N-[4-(4-Bromo-phenyl)-thiazol-2-yl]-4-methyl-benzenesulfonamide

A mixture of 4.0 g of 4-(4-bromophenyl)-thiazol-2-ylamine hydrobromide with 2.5 g of p-toluenesulfonyl chloride was stirred overnight with 15 ml of pyridine. The resulting, red colored suspension was poured into 180 ml of 1N hydrochloric acid and the solid which thereby separated was filtered off and chromatographed on 100 g of Kieselgel 60 with diethyl ether/hexane/methylene chloride (1:1:1) as the eluent. The product-containing fractions were concentrated and the residue was recrystallized twice from 60% ethanol. 0.8 g of N-[4-(4-bromo-phenyl)-thiazol-2-yl]-4-methyl-benzenesulfonamide separated as colorless crystals upon cooling.

M.p.: 227–230° C.

EXAMPLE 16
N-[4-(3-Nitro-phenyl)-thiazol-2-yl]-benzenesulfonamide

A mixture of 0.5 g of 4-(3-nitro-phenyl)-thiazol-2-ylamine hydrobromide with 0.21 g of benzenesulfonyl chloride was stirred overnight with 2 ml of pyridine. The resulting, red colored suspension was poured into 25 ml of 1N hydrochloric acid and the solid which thereby separated was filtered off and dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The product separated as an oil upon neutralization and was thereupon again treated with active charcoal. The product separated upon renewed neutralization with concentrated hydrochloric acid. Recrystallization from 10 ml of 50% ethanol yeilded 0.06 g of N-[4-(3-nitro-phenyl)-thiazol-2-yl]-benzenesulfonamide as yellowish crystals.

M.p.: 141–142° C.

EXAMPLE 17
4-Cyclohexyl-N-[4-(3-nitro-phenyl)-thiazol-2-yl]-benzenesulfonamide A mixture of 0.5 g of 4-(3-nitro-phenyl)-thiazol-2-ylamine hydrobromide with 0.46 g of 4-cyclohexyl-benzenesulfonyl chloride was stirred overnight with 2 ml of pyridine. The resulting, red colored suspension was poured into 25 ml of 1N hydrochloric acid and the organic phase was separated and dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The product separated as an oil upon neutralization. Thereupon, 20 ml of ethanol were added, the mixture was boiled and insoluble material was filtered off. Crystals separated upon cooling and, after recrystallization from 40 ml of 50% ethanol, yielded 0.15 g of 4-cyclohexyl-N-[4-(3-nitro-phenyl)-thiazol-2-yl]-benzenesulfonamide as beige crystals.

M.p.: 180–182° C.

EXAMPLE 18
4-Isopropyl-N-[4-(3-nitro-phenyl)-thiazol-2-yl]-benzenesulfonamide A mixture of 0.5 g of 4-(3-nitro-phenyl)-thiazol-2-ylamine hydrobromide with 0.36 g of 4-isopropylbenzenesulfonyl chloride was stirred overnight with 2 ml of pyridine. The resulting, red colored suspension was poured into 25 ml of 1N hydrochloric acid and the organic phase was separated and dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The product separated as an oil upon neutralization. Thereupon, the mixture was boiled with 0.5 g of active charcoal and the active charcoal and insoluble constituents were filtered off. Crystals separated upon cooling and, after recrystallization from 40 ml of 50% ethanol, yielded 0.17 g of 4-isopropyl-N-[4-(3-nitro-phenyl)-thiazol-2-yl]-benzenesulfonamide as colourless crystals.

M.p.: 144–145° C.

EXAMPLE 19
4-Methyl-N-[4-(4-nitro-phenyl)-thiazol-2-yl]-benzenesulfonamide

A mixture of 0.5 g of 4-(4-nitro-phenyl)-thiazol-2-ylamine hydrobromide with 0.35 g of p-toluenesulfonyl chloride was stirred overnight with 2 ml of pyridine. The resulting, red colored suspension was poured into 30 ml of 1N hydrochloric acid and the mixture was extracted three times with 100 ml of ethyl acetate each time. The organic phases were combined, dried with magnesium sulphate and the solvent was removed on a rotary evaporator. The residue was chromatographed on 60 g of Kieselgel 60 with diethyl ether/ethyl acetate (1:1) as the eluent. The product-containing fractions were concentrated and the residue was digested with a mixture of 20 ml of ethanol and 20 ml of 2N sodium hydroxide solution. The product separated upon neutralization of the filtrate with concentrated hydrochloric acid. Recrystallization from 50 ml of 60% ethanol yielded 0.10 g of 4-methyl-N-[4-(4-nitro-phenyl)-thiazol-2-yl]-benzenesulfonamide as yellowish crystals.
M.p.: >250° C.

EXAMPLE 20
N-{4-[4-(3-Nitro-phenyl)-thiazol-2-ylsulphamoyl]-phenyl}-acetamide A mixture of 0.5 g of 4-(3-nitro-phenyl)-thiazol-2-ylamine hydrobromide with 0.43 g of 4-acetamino-benzenesulfonyl chloride was stirred overnight with 2 ml of pyridine. The resulting, red colored suspension was poured into 30 ml of 1N hydrochloric acid and the solid which thereby separated was filtered off and dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. 0.60 g of N-{4-[4-(3-nitro-phenyl)-thiazol-2-ylsulphamoyl]-phenyl}-acetamide separated as yellowish crystals upon neutralization with concentrated hydrochloric acid.
M.p.: >250° C.

EXAMPLE 21
3,4-Dimethoxy-N-[4-(3-nitro-phenyl)-thiazol-2-yl]-benzenesulfonamide A mixture of 0.5 g of 4-(3-nitro-phenyl)-thiazol-2-ylamine hydrobromide with 0.43 g of 3,4-dimethoxy-benzenesulfonyl chloride was stirred overnight with 2 ml of pyridine. The resulting, red colored suspension was poured into 30 ml of 1N hydrochloric acid and the organic phase was separated and dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The product separated as an oil upon neutralization and was thereupon treated once more with active charcoal. The product separated upon renewed neutralization with concentrated hydrochloric acid. Recrystallization from 25 ml of 60% ethanol yielded 0.12 g of 3,4-dimethoxy-N-[4-(3-nitro-phenyl)-thiazol-2-yl]-benzenesulfonamide as colourless crystals.
M.p.: 185° C.

EXAMPLE 22
5-tert-Butyl-thiophene-2-sulfonic acid [4-(3-nitro-phenyl)-thiazol-2-yl]-amide A mixture of 0.5 g of 4-(3-nitro-phenyl)-thiazol-2-ylamine hydrobromide with 0.43 g of 5-tert-butyl-thiophene-2-sulfonyl chloride was stirred overnight with 2 ml of pyridine. The resulting, red colored suspension was poured into 30 ml of 1N hydrochloric acid and the mixture was extracted three times with 30 ml of ethyl acetate each time. The organic phases were combined, dried with magnesium sulphate and the solvent was removed on a rotary evaporator. The residue was chromatographed on 50 g of Kieselgel 60 with ethyl acetate/hexane (1:2) as the eluent. The product-containing fractions were concentrated and the residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.20 g of 5-tert-butyl-thiophene-2-sulfonic acid [4-(3-nitro-phenyl)-thiazol-2-yl]-amide separated as yellowish crystals after neutralization with concentrated hydrochloric acid and repeated boiling.
M.p.: 176–178° C.

EXAMPLE 23
N-[4-(4-Methoxy-phenyl)-thiazol-2-yl]-4-methyl-benzenesulfonamide A mixture of 0.5 g of 4-(4-methoxy-phenyl)-thiazol-2-ylamine hydrobromide with 0.37 g of p-toluenesulfonyl chloride was stirred overnight with 2 ml of pyridine. The resulting, red colored suspension was poured into 30 ml of 1N hydrochloric acid and the mixture was extracted twice with 40 ml of ethyl acetate each time. The organic phases were combined, dried with magnesium sulphate and the solvent was removed on a rotary evaporator. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 30 ml of 50% ethanol yielded 0.24 g of N-[4-(4-methoxy-phenyl)-thiazol-2-yl]-4-methyl-benzenesulfonamide as beige crystals.
M.p.: 85–88° C. (dec.)

EXAMPLE 24
4-Methyl-N-[4-(3-trifluoromethyl-phenyl)-thiazol-2-yl]-benzenesulfonamide A mixture of 0.5 g of 4-(3-trifluoromethyl-phenyl)-thiazol-2-ylamine hydrobromide with 0.42 g of p-toluenesulfonyl chloride was stirred overnight with 2 ml of pyridine. The resulting, red colored suspension was poured into 30 ml of 1N hydrochloric acid and the mixture was extracted twice with 40 ml of ethyl acetate each time. The organic phases were combined, dried with magnesium sulphate and the solvent was removed on a rotary evaporator. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.23 g of 4-methyl-N-[4-(3-trifluoromethyl-phenyl)-thiazol-2-yl]-benzenesulfonamide separated as colorless crystals upon neutralization with concentrated hydrochloric acid.
M.p.: 157–159° C.

EXAMPLE 25

4-Methyl-N-[4-(4-methyl-phenyl)-thiazol-2-yl]-benzenesulfonamide

A mixture of 0.5 g 4-(4-methyl-phenyl)-thiazol-2-ylamine hydrobromide with 0.39 g of p-toluenesulfonyl chloride was stirred overnight with 2 ml of pyridine. The resulting, red colored suspension was poured into 30 ml of 1N hydrochloric acid and the mixture was extracted twice with 50 ml of ethyl acetate each time. The organic phases were combined, dried with magnesium sulphate and the solvent was removed on a rotary evaporator. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.46 g of 4-methyl-N-[4-(4-methyl-phenyl)-thiazol-2-yl]-benzenesulfonamide was obtained as colorless crystals upon neutralization with concentrated hydrochloric acid.

M.p.: 186–189° C.

EXAMPLE 26

4-Methyl-N-[4-(2-nitro-phenyl)-thiazol-2-yl]-benzenesulfonamide

A mixture of 0.5 g of 4-(2-nitro-phenyl)-thiazol-2-ylamine hydrobromide with 0.47 g of p-toluenesulfonyl chloride was stirred overnight with 2 ml of pyridine. The resulting, red colored suspension was poured into 30 ml of 1N hydrochloric acid and extracted twice with 40 ml of ethyl acetate each time. The organic extracts were combined, dried with magnesium sulphate and concentrated. The residue was dissolved in a mixture of 30 ml of ethanol and 20 ml of 2N sodium hydroxide solution. After the addition of 0.4 g of active charcoal the mixture was stirred at room temperature for 30 minutes and subsequently the active charcoal was filtered off. After neutralization with concentrated hydrochloric acid and boiling there separated, upon cooling, 0.58 g of 4-methyl-N-[4-(2-nitro-phenyl)-thiazol-2-yl]-benzenesulfonamide as yellow crystals.

M.p.: 172–174° C.

EXAMPLE 27

4-Methyl-N-(4-naphthalen-1-yl-thiazol-2-yl)-benzenesulfonamide

A mixture of 0.5 g of 4-(1-naphthyl)-thiazol-2-ylamine hydrobromide with 0.34 g of p-toluenesulfonyl chloride was stirred overnight with 2 ml of pyridine. The resulting, red colored suspension was poured into 30 ml of 1N hydrochloric acid and extracted twice with 40 ml of ethyl acetate each time. The organic extracts were combined, dried with magnesium sulphate and concentrated. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 60 ml of 50% ethanol yielded 0.46 g of 4-methyl-N-(4-naphthalen-1-yl-thiazol-2-yl)-benzenesulfonamide as colorless crystals.

M.p.: 196–197° C.

EXAMPLE 28

N-[4-(3,4-Dichloro-phenyl)-thiazol-2-yl]-4-methyl-benzenesulfonamide

A mixture of 0.5 g of 4-(3,4-dichloro-phenyl)-thiazol-2-ylamine hydrobromide with 0.50 g of p-toluenesulfonyl chloride was stirred overnight with 2 ml of pyridine. The resulting, red colored suspension was poured into 30 ml of 1N hydrochloric acid and the solid which thereby separated was filtered off and dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.33 g of N-[4-(3,4-dichloro-phenyl)-thiazol-2-yl]-4-methyl-benzenesulfonamide was obtained as colorless crystals upon neutralization with concentrated hydrochloric acid.

M.p.: 205–206° C.

EXAMPLE 29

N-[4-(2,4-Dichloro-phenyl)-thiazol-2-yl]-4-methyl-benzenesulfonamide

A mixture of 0.5 g of 4-(2,4-dichloro-phenyl)-thiazol-2-ylamine hydrobromide with 0.32 g of p-toluenesulfonyl chloride was stirred overnight with 2 ml of pyridine. The resulting, red colored suspension was poured into 30 ml of 1N hydrochloric acid and extracted three times with 40 ml of ethyl acetate each time. The organic extracts were combined, dried with magnesium sulphate and concentrated. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.50 g of N-[4-(2,4-dichloro-phenyl)-thiazol-2-yl]-4-methyl-benzenesulfonamide separated as colorless crystals upon neutralization with concentrated hydrochloric acid.

M.p.: 218–219° C.

EXAMPLE 30

N-[4-(3-Bromo-phenyl)-thiazol-2-yl]-4-methyl-benzenesulfonamide

A mixture of 0.5 g of 4-(3-bromo-phenyl)-thiazol-2-ylamine hydrobromide with 0.31 g of p-toluenesulfonyl chloride was stirred overnight with 2 ml of pyridine. The resulting, red colored suspension was poured into 30 ml of 1N hydrochloric acid and the solid which thereby separated was filtered off and dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.40 g of N-[4-(3-bromo-phenyl)-thiazol-2-yl]-4-methyl-benzenesulfonamide separated as colorless crystals upon neutralization with concentrated hydrochloric acid.

M.p.: 199–200° C.

EXAMPLE 31

4-Amino-N-[4-(3-nitro-phenyl)-thiazol-2-yl]-benzenesulfonamide 0.47 g of N-{4-[4-(3-nitro-phenyl)-thiazol-2-ylsulphamoyl]-phenyl}-acetamide was suspended in 10 ml of 6N hydrochloric acid and heated to boiling overnight. The cooled mixture was treated with 35 ml of 2N sodium hydroxide solution. After the addition of 0.4 g of active charcoal the mixture was stirred at room temperature for 30 minutes and subsequently the active charcoal was filtered off. The product separated upon neutralization with concentrated hydrochloric acid. Recrystallization from 50 ml of 40% ethanol yielded 0.16 g of 4-amino-N-[4-(3-nitro-phenyl)-thiazol-2-yl]-benzenesulfonamide as yellowish crystals.
M.p.: 191–193° C.

EXAMPLE 32
N-[4-(2-Fluoro-5-trifluoromethyl-phenyl)-thiazol-2-yl]-4-methyl-benzenesulfonamide A mixture of 0.5 g of 4-(2-fluoro-5-trifluoromethyl-phenyl)-thiazol-2-ylamine hydrobromide with 0.30 g of p-toluenesulfonyl chloride was stirred for 3 hours with 2 ml of pyridine. The resulting, red colored suspension was poured into 30 ml of 1N hydrochloric acid and the mixture was extracted with ethyl acetate. The organic phase was dried with magnesium sulphate and concentrated. The residue was dissolved in a mixture of 20 ml of ethanol and 20 ml of 2N sodium hydroxide solution. After the addition of 0.3 g of active charcoal the mixture was stirred at room temperature for 30 minutes and subsequently the active charcoal was filtered off. 0.36 g of N-[4-(2-fluoro-5-trifluoromethyl-phenyl)-thiazol-2-yl]-4-methyl-benzenesulfonamide separated as colorless crystals upon neutralization with concentrated hydrochloric acid.
M.p.: 136–140° C.

EXAMPLE 33
4-Benzyloxy-N-[4-(3-nitro-phenyl)-thiazol-2-yl]-benzenesulfonamide A mixture of 0.5 g of 4-(3-nitro-phenyl)-thiazol-2-ylamine hydrobromide with 0.51 g of 4-phenylmethoxy-benzenesulfonyl chloride was stirred overnight with 2 ml of pyridine. The resulting, red colored suspension was poured into 30 ml of 1N hydrochloric acid. The mixture was extracted three times with ethyl acetate. The organic phases were combined, dried with magnesium sulphate and freed from solvent. The residue was boiled with 30 ml of ethyl acetate, insoluble constituents were filtered off and the solution was treated at boiling with 20 ml of hexane. 0.5 g of 4-benzyloxy-N-[4-(3-nitro-phenyl)-thiazol-2-yl]-benzenesulfonamide separated as beige crystals upon cooling.
M.p.: 214–216° C.

EXAMPLE 34
N-[4-(3-Nitro-phenyl)-thiazol-2-yl]-C-phenyl-methanesulfonamide

A mixture of 0.5 g of 4-(3-nitro-phenyl)-thiazol-2-ylamine hydrobromide with 0.35 g of phenylmethanesulfonyl chloride was stirred overnight with 2 ml of pyridine. The resulting, red colored suspension was poured into 30 ml of 1N hydrochloric acid and the solid which thereby separated was filtered off and dissolved in a mixture of 25 ml of ethanol and 20 ml of 2N sodium hydroxide solution. After the addition of 0.4 g of active charcoal the mixture was stirred at room temperature for 30 minutes and subsequently the active charcoal was filtered off. After neutralization with concentrated hydrochloric acid the mixture was concentrated and the aqueous residue was extracted twice with ethyl acetate. The organic phases were combined, dried with magnesium sulphate and freed from solvent. The residue was chromatographed on 30 g of Kieselgel 60 with ethyl acetate/hexane (1:2) as the eluent. The product-containing fractions were concentrated. Recrystallization of the residue from 5 ml of ethyl acetate yielded 60 mg of N-[4-(3-nitro-phenyl)-thiazol-2-yl]-C-phenyl-methanesulfonamide as colorless crystals.
M.p.: 219–221° C.

EXAMPLE 35
N-[4-(4-Cyclohexyl-phenyl)-thiazol-2-yl]-4-methyl-benzenesulfonamide A mixture of 0.5 g of 4-(4-cyclohexyl-phenyl)-thiazol-2-ylamine hydrobromide with 0.31 g of p-toluenesulfonyl chloride was stirred for 3 hours with 2 ml of pyridine. The resulting, red colored suspension was poured into 30 ml of 1N hydrochloric acid and the mixture was extracted with ethyl acetate. The organic phase was dried with magnesium sulphate and concentrated. The residue was dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The product separated in amorphous form upon neutralization with concentrated hydrochloric acid. After chromatography on 70 g of Kieselgel 60 with ethyl acetate/hexane (1:2) the product-containing fractions were concentrated. Recrystallization from 50% ethanol yielded 0.22 g of N-[4-(4-cyclohexyl-phenyl)-thiazol-2-yl]-4-methyl-benzenesulfonamide as colorless crystals.
M.p.: 197–199° C.

EXAMPLE 36
N-[4-(3-Fluoro-5-trifluoromethyl-phenyl)-thiazol-2-yl]-4-methyl-benzenesulfonamide A mixture of 0.5 g of 4-(3-fluoro-5-trifluoromethyl-phenyl)-thiazol-2-ylamine hydrobromide with 0.34 g of p-toluenesulfonyl chloride was stirred overnight with 2 ml of pyridine. The resulting, red colored suspension was poured into 30 ml of 1N hydrochloric acid and the mixture was extracted with ethyl acetate. The organic phase was dried with magnesium sulphate and concentrated. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. 0.38 g of N-[4-(3-fluoro-5-trifluoromethyl-phenyl)-thiazol-2-yl]-4-methyl-benzenesulfonamide separated as colorless crystals upon neutralization with concentrated hydrochloric acid.
M.p.: 165–167° C.

EXAMPLE 37
N-[4-(2-Benzyloxy-phenyl)-thiazol-2-yl]-4-methyl-benzenesulfonamide A mixture of 0.5 g of 4-(2-benzyloxy-phenyl)-thiazol-2-ylamine hydrobromide with 0.29 g of p-toluenesulfonyl chloride was stirred for 2 hours with 2 ml of pyridine. The resulting, red colored suspension was poured into 30 ml of 1N hydrochloric acid and the mixture was extracted with ethyl acetate. The organic phase was dried with magnesium sulphate and concentrated. The residue was dissolved in a mixture of 20 ml of ethanol and 20 ml of 2N sodium hydroxide solution. After the addition of 0.4 g of active charcoal the mixture was stirred at room temperature for 30 minutes and subsequently the active charcoal was filtered off. After neutralization with concentrated hydrochloric acid the mixture was concentrated and the aqueous residue was extracted twice with ethyl acetate. The organic phases were combined, dried with magnesium sulphate and freed from solvent. The residue was chromatographed on 60 g of Kieselgel 60 with ethyl acetate/hexane (1:2) as the eluent. The product-containing fractions were concentrated and yielded 0.28 g of N-[4-(2-benzyloxy-phenyl)-thiazol-2-yl]-4-methyl-benzenesulfonamide as a colorless, amorphous solid.

NMR (CDCl$_3$) ppm: 10.5 (bs, 1H), 7.83 (d, 2H), 7.48 ("d", 1H), 7.34 (m, 6H) 7.25 (d, 2H), 7.03 ("t", 2H), 6.59 (s, 1H), 5.26 (s, 2H), 2.40 (s, 3H).

EXAMPLE 38
N-[4-(3-Benzyloxy-phenyl)-thiazol-2-yl]-4-methyl-benzenesulfonamide A mixture of 3.0 g of 4-(3-benzyloxy-phenyl)-thiazol-2-ylamine hydrobromide with 1.8 g of p-toluenesulfonyl chloride was stirred for 2 hours with 12 ml of pyridine. The resulting, red colored suspension was poured into 100 ml of 2N hydrochloric acid and the mixture was extracted with ethyl acetate. The organic phase was dried with magnesium sulphate and concentrated. The residue was dissolved in a mixture of 120 ml of ethanol and 120 ml of 2N sodium hydroxide solution. After the addition of 2.4 g of active charcoal the mixture was stirred at room temperature for 30 minutes and subsequently the active charcoal was filtered off. After neutralization with concentrated hydrochloric acid the mixture was concentrated and the aqueous residue was extracted twice with ethyl acetate. The organic phases were combined, dried with magnesium sulphate and freed from solvent. The residue was chromatographed on 300 g of Kieselgel 60 with ethyl acetate/hexane (1:2) as the eluent. The product-containing fractions were concentrated and yielded 2.2 g of N-[4-(3-benzyloxy-phenyl)-thiazol-2-yl]-4-methyl-benzenesulfonamide as a colorless, amorphous solid.

NMR (CDCl$_3$) ppm: 9.6 (bs, 1H), 7.85 (d, 2H), 7.36 (m, 6H) 7.24 (d, 2H), 7.01 (m, 3H), 6.50 (s, 1H), 5.08 (s, 2H), 2.39 (s, 3H).

EXAMPLE 39
N-[4-(3-Amino-phenyl)-thiazol-2-yl]-4-methyl-benzenesulfonamide

A solution of 1.5 g of 4-methyl-N-[4-(3-nitro-phenyl)-thiazol-2-yl]-benzenesulfonamide in 150 ml of methanol and 70 ml of ethyl acetate was hydrogenated at room temperature after the addition of 0.15 g of palladium on active charcoal (10%). The catalyst was filtered off and the filtrate was concentrated. Crystallization from ethyl acetate/hexane (1:1) yielded 1.1 g of N-[4-(3-amino-phenyl)-thiazol-2-yl]-4-methyl-benzenesulfonamide as a colorless solid.

M.p.: 180–182° C.

EXAMPLE 40
N-(4-Biphenyl-3-yl-thiazol-2-yl)-4-methyl-benzenesulfonamide

A solution of 0.29 g of N-(4-biphenyl-3-yl-thiazol-2-yl)-N-methoxymethyl-4-methyl-benzenesulfonamide in 6 ml of tetrahydrofuran was stirred at room temperature for 6 hours after the addition of 1.5 ml of 6N hydrochloric acid. The reaction mixture was added to 40 ml of water and extracted with ethyl acetate. The organic phases were combined, dried with magnesium sulphate and concentrated. Recrystallization from 10 ml of 50% ethanol yielded 120 mg of N-(4-biphenyl-3-yl-thiazol-2-yl)-4-methyl-benzenesulfonamide as colorless crystals.

M.p.: 153–155° C.

EXAMPLE 41
N-[4-(2-Fluoro-5-trifluoromethyl-phenyl)-thiazol-2-yl]4-methoxy-benzenesulfonamide A mixture of 0.5 g of 4-(2-fluoro-5-trifluoromethyl-phenyl)-thiazol-2-ylamine hydrobromide with 0.33 g of 4-methoxy-benzenesulfonyl chloride was stirred overnight with 2 ml of pyridine. The resulting, red colored suspension was poured into 30 ml of 1N hydrochloric acid and the mixture was extracted lo with ethyl acetate. The organic phase was dried with magnesium sulphate and concentrated. The residue was dissolved in a mixture of 30 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 30 ml of 50% ethanol yielded 0.26 g of N-[4-(2-fluoro-5-trifluoromethyl-phenyl)-thiazol-2-yl]-4-methoxy-benzenesulfonamide as colorless crystals.

M.p.: 112° C. dec.

EXAMPLE 42
4-Amino-N-[4-(2-fluoro-5-trifluoromethyl-phenyl)-thiazol-2-yl]benzene-sulfonamide A mixture of 0.5 g of 4-(2-fluoro-5-trifluoromethyl-phenyl)-thiazol-2-ylamine hydrobromide with 0.38 g of 4-acetaminobenzenesulfonyl chloride was stirred for 2 hours with 2 ml of pyridine. The resulting, red colored suspension was poured into 30 ml of 1N hydrochloric acid and stirred at room temperature for 30 minutes. The separated solid was dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. The 4-acetamino-N-[4-(2-fluoro-5-trifluoromethyl-phenyl)-thiazol-2-yl]-benzenesulfonamide, which separated upon neutralization with concentrated hydrochloric acid, was suspended in 9 ml of 6N hydrochloric acid and boiled for 36 hours. The mixture was cooled, treated with 30 ml of ethanol and neutralized with 2N sodium hydroxide solution. Recrystallization of the product, which thereby separated, from 20 ml of 50% ethanol yielded 0.21 g of 4-amino-N-[4-(2-fluoro-5-trifluoromethyl-phenyl)-thiazol-2-yl]benzenesulfonamide as colorless crystals.

M.p.: 150–152° C.

EXAMPLE 43

N-[4-(4-Benzyloxy-phenyl)-thiazol-2-yl]4-methyl-benzenesulfonamide

A mixture of 0.5 g of 4-(4-benzyloxy-phenyl)-thiazol-2-ylamine hydrobromide with 0.29 g of p-toluenesulfonyl chloride was stirred for 4 hours with 2 ml of pyridine. The resulting, red colored suspension was poured into 30 ml of 1N hydrochloric acid and the mixture was extracted with methylene chloride. The organic phase was dried with magnesium sulphate and concentrated. The residue was dissolved in a mixture of 20 ml of ethanol and 20 ml of 2N sodium hydroxide solution. After the addition of 0.7 g of active charcoal the mixture was stirred at room temperature for 30 minutes and subsequently the active charcoal was filtered off. After neutralization with concentrated hydrochloric acid the mixture was concentrated and the residue was chromatographed on 100 g of Kieselgel 60 with diethyl ether as the eluent. The product-containing fractions were concentrated and, after recrystallization from ethyl acetate, yielded 0.22 g of N-[4-(4-benzyloxy-phenyl)-thiazol-2-yl]-4-methyl-benzenesulfonamide as colorless crystals.
M.p.: 166–167° C.

EXAMPLE 44

4-Methoxy-N-(4-naphthalen-2-yl-thiazol-2-yl)-benzenesulfonamide

A mixture of 0.5 g of 4-(2-naphthyl)-thiazol-2-ylamine hydrobromide with 0.34 g of 4-methoxy-benzenesulfonyl chloride was stirred for 3 hours with 2 ml of pyridine. The resulting, red colored suspension was poured into 30 ml of 1N hydrochloric acid and extracted with ethyl acetate. The organic phases were combined, dried with magnesium sulphate and freed from solvent. The residue was dissolved in a mixture of 25 ml of ethanol and 20 ml of 2N sodium hydroxide solution. After the addition of 0.5 g of active charcoal the mixture was stirred at room temperature for 30 minutes and subsequently the active charcoal was filtered off. The product separated upon neutralization with concentrated hydrochloric acid. Recrystallization from 10 ml of ethyl acetate and 15 ml of n-hexane yielded 0.19 g of 4-methoxy-N-(4-naphthalen-2-yl-thiazol-2-yl)-benzenesulfonamide as colorless crystals.
M.p.: 163–165° C.

EXAMPLE 45

N-[4-(3,4-Dihydroxy-5-nitro-phenyl)-thiazol-2-yl]4-methyl-benzenesulfonamide A mixture of 0.24 g of N-(aminothioxomethyl)-4-methyl-benzene-sulfonamide and 0.2 g of 2-bromo-1-(3,4-dihydroxy-5-nitrophenyl)ethanone was dissolved in 5 ml of ethanol and boiled under reflux for 1 h. 0.26 g of N-[4-(3,4-dihydroxy-5-nitro-phenyl)-thiazol-2-yl]-4-methyl-benzenesulfonamide separated as red crystals upon cooling.
M.p.: 252–254° C. (dec.)

EXAMPLE 46

3,4-Dimethoxy-N-[4-(2-fluoro-5-trifluoromethyl-phenyl)-thiazol-2-yl]benzenesulfonamide A mixture of 0.5 g of 4-(2-fluoro-5-trifluoromethyl-phenyl)-thiazol-2-ylamine hydrobromide with 0.38 g of 3,4-dimethoxy-benzenesulfonyl chloride was stirred overnight with 2 ml of pyridine. The resulting, red colored suspension was poured into 30 ml of 1N hydrochloric acid and the mixture was extracted with ethyl acetate. The organic phase was dried with magnesium sulphate and concentrated. The residue was dissolved in a mixture of 20 ml of ethanol and 20 ml of 2N sodium hydroxide solution. After the addition of 0.5 g of active charcoal the mixture was stirred at room temperature for 30 minutes and subsequently the active charcoal was filtered off. After neutralization with concentrated hydrochloric acid the mixture was concentrated and the residue was chromatographed on 40 g of Kieselgel 60 with ethyl acetate/hexane (1:1) as the eluent. The product-containing fractions were concentrated and, after recrystallization from 15 ml of 50% ethanol, yielded 0.16 g of N-[4-(3-fluoro-5-trifluoromethyl-phenyl)-thiazol-2-yl]-4-methyl-benzenesulfonamide as colorless crystals.
M.p.: 123–125° C.

EXAMPLE 47

3-Bromo-4-methoxy-N-[4-(3-nitro-phenyl)-thiazol-2-yl]-benzenesulfonamide

A mixture of 5.0 g of 4-(3-nitro-phenyl)-thiazol-2-ylamine hydrobromide with 5.2 g of 3-bromo-4-methoxy-benzene-sulfonyl chloride was stirred for 3 hours with 20 ml of pyridine. The resulting, red colored suspension was poured into 300 ml of 1N hydrochloric acid and the mixture was extracted with ethyl acetate. The organic phase was dried with magnesium sulphate and concentrated. The residue was dissolved in a mixture of 300 ml of ethanol and 200 ml of 2N sodium hydroxide solution. After the addition of 4.5 g of active charcoal the mixture was stirred at room temperature for 30 minutes and subsequently the active charcoal was filtered off. 4.4 g of 3-bromo-4-methoxy-N-[4-(3-nitro-phenyl)-thiazol-2-yl]-benzenesulfonamide separated as yellow crystals upon neutralization with concentrated hydrochloric acid.
M.p.: 200–202° C.

EXAMPLE 48

N-[4-(3-Hydroxy-4-methoxy-5-nitro-phenyl)-thiazol-2-yl]-4-methyl-benzenesulfonamide 50 mg of sodium hydride (60%) were added to a solution of 0.5 g of N-[4-(3,4-dihydroxy-5-nitro-phenyl)-thiazol-2-yl]-4-methyl-benzenesulfonamide in 5 ml of dimethylformamide. The mixture was stirred at room temperature for 1 hour. The reaction mixture was poured into water and extracted with ethyl acetate. The organic phase was dried with magnesium sulphate and concentrated. The residue was chromatographed on 60 g of Kieselgel 60 with methylene chloride/acetone/formic acid (90:10:2.5) as the eluent. The product-containing fractions were concentrated and, after boiling with 20 ml of diethyl ether, yielded 0.17 g of N-[4-(3-hydroxy-4-methoxy-5-nitro-phenyl)-thiazol-2-yl]-4-methyl-benzenesulfonamide as orange colored crystals.
M.p.: 210–212° C.

EXAMPLE 49

3,4-Dimethoxy-N-(4-naphthalen-1-yl-thiazol-2-yl)-benzenesulfonamide

A mixture of 10 g of 4-(1-naphthyl)-thiazol-2-ylamine hydrobromide with 8.5 g of 3,4-dimethoxy-benzenesulfonyl chloride was stirred for 18 hours with 30 ml of pyridine. The resulting, red colored suspension was poured into 400 ml of 1N hydrochloric acid. The separated solid was dissolved in a mixture of 400 ml of ethanol and 400 ml of 2N sodium hydroxide solution. After the addition of 8 g of active charcoal the mixture was stirred at room temperature for 30 minutes and subsequently the active charcoal was filtered off. After neutralization with concentrated hydrochloric acid the mixture was concentrated and the residue was taken up with ethyl acetate, dried with magnesium sulphate and concentrated. Crystallization from 200 ml of ethyl acetate yielded 11.5 g of 3,4-dimethoxy-N-(4-naphthalen-1-yl-thiazol-2-yl)-benzenesulfonamide as colorless crystals.
M.p.: 132–133° C.

EXAMPLE 50
3,4-Dimethoxy-N-(4-naphthalen-2-yl-thiazol-2-yl)-benzenesulfonamide A mixture of 10 g of 4-(2-naphthyl)-thiazol-2-ylamine hydrobromide with 8.5 g of 3,4-dimethoxy-benzenesulfonyl chloride was stirred for 18 hours with 40 ml of pyridine. The resulting, red colored suspension was poured into 400 ml of 1N hydrochloric acid and the mixture was extracted with ethyl acetate. The organic phase was dried with magnesium sulphate and (sic) concentrated. The residue was dissolved in a mixture of 500 ml of ethanol and 400 ml of 2N sodium hydroxide solution. After the addition of 10 g of active charcoal the mixture was stirred at room temperature for 30 minutes and subsequently the active charcoal was filtered off. 11.1 g of 3,4-dimethoxy-N-(4-naphthalen-2-yl-thiazol-2-yl)-benzenesulfonamide separated upon neutralization with concentrated hydrochloric acid in the form of colorless crystals, which were recrystallized from ethanol/water.
M.p.: 114–117° C.

EXAMPLE 51
4-Methoxy-N-(4-naphthalen-1-yl-thiazol-2-yl)-benzenesulfonamide

A mixture of 10 g of 4-(1-naphthyl)-thiazol-2-ylamine hydrobromide with 7.4 g of 4-methoxy-benzenesulfonyl chloride was stirred for 16 hours with 40 ml of pyridine. The resulting, red colored suspension was poured into 400 ml of 1N hydrochloric acid and the extracted with ethyl acetate. The organic phases were combined, dried with magnesium sulphate and free from solvent. The residue was dissolved in a mixture of 500 ml of ethanol and 400 ml of 2N sodium hydroxide solution. After the addition of 10 g of active charcoal the mixture was stirred at room temperature for 30 minutes and subsequently the active charcoal was filtered off. After neutralization with concentrated hydrochloric acid the mixture was concentrated, the residue was taken up with ethyl acetate, dried with magnesium sulphate and concentrated. Crystallization from ethyl acetate/hexane yielded 10.2 g of 4-methoxy-N-(4-naphthalen-1-yl-thiazol-2-yl)-benzenesulfonamide as colorless crystals, which were recrystallized once from ethyl acetate/hexane.
M.p.: 98–100° C.
Intermediates

EXAMPLE 52
3-(2-Amino-thiazol-4-yl)-benzonitrile 16.9 g of 3-bromoacetyl-benzonitrile were placed in 50 ml of methanol and treated at room temperature with 8 g of thiourea. The mixture was boiled for 2½ hours and then cooled to 0° C. while stirring slowly. The product separated as the salt, was filtered off and converted into the base by the addition of 100 ml of 2N sodium hydroxide solution. The aqueous suspension was extracted with a total of 700 ml of methylene chloride and the organic phase was dried with magnesium sulphate. 9.6 g of 3-(2-amino-thiazol-4-yl)-benzonitrile separated upon concentration.
M.p.: 195–198° C.

EXAMPLE 53
4-Cyclohexyl-benzenesulfonyl chloride

A solution of 10.6 ml of phenylcyclohexane in 100 ml of methylene chloride was added at 5° C. within 30 minutes to 13.8 ml of chlorosulfonic acid. The mixture was stirred at 5° C. for 1 hour, poured into 400 ml of a 20% ammonium chloride solution and extracted twice with 300 ml of methylene chloride each time. The organic phases were combined, dried with magnesium sulphate and the solvent was removed on a rotary evaporator. 13.6 g of 4-cyclohexyl-benzenesulfonyl chloride separated as a reddish oil, which was used without further purification.
NMR (CDCl$_3$) ppm: 7.94 (d, 2H), 7.43 (d, 2H), 2.62 (m, 1H), 2.0–1.2 (m, 10 H)

EXAMPLE 54
4-Isopropyl-benzenesulfonyl chloride

A solution of 11.6 ml of isopropylbenzene in 100 ml of methylene chloride was added at 5° C. within 30 minutes to 18.3 ml of chlorosulfonic acid. The reaction mixture was stirred at 5° C. for 1 hour, poured on to 500 ml of ice-water and, after stirring for 5 minutes, treated with 100 g of ammonium chloride. After extraction with methylene chloride (1×800 ml, 1×500 ml) the organic phases were combined, dried with magnesium sulphate and the solvent was removed on a rotary evaporator. 12.3 g of 4-isopropyl-benzenesulfonyl chloride separated as a reddish oil, which was used without further purification.
NMR (CDCl$_3$) ppm: 7.96 (d, 2H), 7.46 (d, 2H), 3.04 (m, 1H), 1.30 (d, 6 H)

EXAMPLE 55
4-(3-Trifluoromethyl-phenyl)-thiazol-2-ylamine hydrobromide

A solution of 8.1 g of 2-bromo-1-(3-trifluoromethyl-phenyl)-ethanone in 70 ml of methanol was treated at room temperature with 3.2 g of thiourea and boiled for 1 hour. 4.1 g of 4-(3-trifluoromethyl-phenyl)-thiazol-2-ylamine hydrobromide separated as colorless crystals upon cooling to 0° C.
M.p.: 206–208° C.

EXAMPLE 56
4-(4-Benzyloxy-3-methoxy-phenyl)-thiazol-2-ylamine hydrobromide 4-(4-Benzyloxy-3-methoxy-phenyl)-thiazol-2-yl-amine hydrobromide was prepared in all respects analogously from 2-bromo-1-(4-benzyloxy-3-methoxy-phenyl)-ethanone.
M.p.: 239–240° C.

EXAMPLE 57
4-(3,4-Bis-benzyloxy-phenyl)-thiazol-2-ylamine hydrobromide 4-(3,4-Bis-benzyloxy-phenyl)-thiazol-2-ylamine hydrobromide was prepared in all respects analogously from 2-bromo-1-(3,4-bis-benzyloxy-phenyl)-ethanone.
M.p.: 166–167° C.

EXAMPLE 58
2-Bromo-1-(2-fluoro-5-trifluoromethyl-phenyl)-ethanone

A solution of 5.0 g of 2-fluoro-5-trifluoromethyl-acetophenone in 35 ml of acetic acid was treated with 0.8 ml of bromine at room temperature within 10 minutes. The brown color disappeared after stirring at room temperature for 3 hours. The reaction mixture was added to 150 ml of ice-water and extracted twice with diethyl ether. The organic phases were washed twice with saturated sodium bicarbonate solution, combined, dried with sodium sulphate and concentrated. The residue weighed 5.8 g, contained about 60% of 2-bromo-1-(2-fluoro-5-trifluoromethyl-phenyl)-ethanone and was processed without purification.

EXAMPLE 59
4-(2-Fluoro-5-trifluoromethyl-phenyl)-thiazol-2-ylamine hydrobromide A solution of 5.8 g of 2-bromo-1-(2-fluoro-5-trifluoromethyl-phenyl)-ethanone in 44 ml of methanol was treated at room temperature with 2.2 g of thiourea and boiled for 1 hour. 2.8 g of 4-(2-fluoro-5-trifluoromethyl-phenyl)-thiazol-2-ylamine hydrobromide separated as colorless crystals upon cooling to 0° C. and after the addition of 15 ml of diethyl ether.
M.p.: 194–195° C.

EXAMPLE 60
2-Bromo-1-(3-fluoro-5-trifluoromethyl-phenyl)-ethanone

A solution of 5.8 g of 3-fluoro-5-trifluoromethyl-acetophenone in 35 ml of acetic acid was treated with 0.94 ml of bromine at room temperature within 10 minutes. The brown color disappeared after stirring at room temperature for 2 hours. The reaction mixture was added to 150 ml of ice-water and extracted twice with diethyl ether. The organic phases were washed twice with saturated sodium bicarbonate solution, combined, dried with magnesium sulphate and concentrated. The residue weighed 7.2 g, contained about 60% of 2-bromo-1-(3-fluoro-5-trifluoromethyl-phenyl)-ethanone and was processed without further purification.

EXAMPLE 61
4-(3-Fluoro-5-trifluoromethyl-phenyl)-thiazol-2-ylamine hydrobromide A solution of 7.2 g of 2-bromo-1-(3-fluoro-5-trifluoromethyl-phenyl)-ethanone in 60 ml of methanol was treated at room temperature with 2.7 g of thiourea and boiled for 1 hour. 5.2 g of 4-(3-fluoro-5-trifluoromethyl-phenyl)-thiazol-2-ylamine hydrobromide separated as colorless crystals upon cooling to 0° C. and after the addition of 15 ml of diethyl ether.
M.p.: 219–221° C.

EXAMPLE 62
4-(2-Benzyloxy-phenyl)-thiazol-2-ylamine hydrobromide

A solution of 21.7 g of 2-bromo-1-(2-benzyloxy-phenyl)-ethanone in 150 ml of methanol was treated at room temperature with 7.6 g of thiourea and boiled for 1 hour. The reaction mixture was concentrated to a volume of 60 ml. 20.7 g of 4-(2-benzyloxy-phenyl)-thiazol-2-ylamine hydrobromide separated as colorless crystals upon cooling to 0° C. and after the addition of 250 ml of diethyl ether.
M.p.: 194–196° C.

EXAMPLE 63
4-(3-Benzyloxy-phenyl)-thiazol-2-ylamine hydrobromide

A solution of 22.5 g of 2-bromo-1-(3-benzyloxy-phenyl)-ethanone in 150 ml of methanol was treated at room temperature with 7.8 g of thiourea and boiled for 1 hour. 16.1 g of 4-(3-benzyloxy-phenyl)-thiazol-2-ylamine hydrobromide separated as colorless crystals upon cooling to 0° C.
M.p.: 168–170° C.

EXAMPLE 64
N-[4-(3-Bromo-phenyl)-thiazol-2-yl]-N-methoxymethyl-4-methyl-benzenesulfonamide A solution of 0.72 g of N-[4-(3-bromo-phenyl)-thiazol-2-yl]-4-methyl-benzenesulfonamide and 0.6 ml of ethyldiisopropylamine in 10 ml of methylene chloride was cooled to 0° C. and, after the addition of 0.13 ml of chloromethyl methyl ether, stirred at 0° C. for 2 h. Thereafter, the mixture was treated with 40 ml of water and extracted with methylene chloride. The organic phase was dried with magnesium sulphate and concentrated. After chromatography on 60 g of Kieselgel 60 with ethyl acetate/hexane (1:3) as the eluent the product-containing fractions were concentrated. 0.64 g of colorless N-[4-(3-bromo-phenyl)-thiazol-2-yl]-N-methoxymethyl-4-methyl-benzenesulfonamide, obtained in amorphous form, was processed without further purification.
NMR (CDCl$_3$) ppm: 7.89 (s, 1H), 7.85 (d, 2H), 7.56 (d, 1H), 7.38 (d, 1H) 7.31 (d, 2H), 7.23 (dd, 1H), 7.18 (s, 1H), 5.51 (s, 2H), 3.47 (s, 3H), 2.42 (s, 3H).

EXAMPLE 65
N-(4-Biphenyl-3-yl-thiazol-2-yl)-N-methoxymethyl-4-methyl-benzenesulfonamide A solution of 0.5 g of N-[4-(3-bromo-phenyl)-thiazol-2-yl]-N-methoxymethyl-4-methyl-benzenesulfonamide in 8 ml of toluene was treated in succession with 0.1 g of anhydrous lithium chloride, 60 mg of tetrakis (triphenylphosphine)palladium, 0.23 g of phenylboric acid and 2 ml of 2N potassium carbonate solution. The mixture was boiled overnight, cooled and, after the addition of water, extracted with ethyl acetate. The organic phases were combined, dried with magnesium sulphate and concentrated. The residue was chromatographed on 80 g of Kieselgel 60 with ethyl acetate/hexane (1:4) as the eluent. The product-containing fractions were concentrated and yielded 0.29 g of colorless, amorphous N-(4-biphenyl-3-yl-thiazol-2-yl)-N-methoxymethyl-4-methyl-benzenesulfonamide, which was processed without further purification.
NMR (CDCl$_3$) ppm: 7.99 (s, 1H), 7.86 (d, 2H), 7.72 (d, 1H), 7.6–7.2 (m, 9H), 6.80 (d, 1H), 5.53 (s, 2H), 3.48 (s, 3H), 2.38 (s, 3H).

EXAMPLE A

Tablets of the following composition are produced in the usual manner:

|  | mg/tablet |
|---|---|
| White corn starch | 100 |
| Powd. Lactose | 95 |
| White corn starch | 35 |
| Polyvinylpyrrolidone | 8 |
| Na carboxymethylstarch | 10 |

-continued

| | mg/tablet |
|---|---|
| Magnesium stearate | 2 |
| Tablet weight | 250 |

EXAMPLE B

Tablets of the following composition are produced in the usual manner:

| | mg/tablet |
|---|---|
| White corn starch | 200 |
| Powd. Lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| | mg/capsule |
|---|---|
| White corn starch | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

We claim:

1. A method of inhibiting kynurenin-3-hydroxylase comprising administering to a host in need of such inhibition an effective amount of a compound of the formula

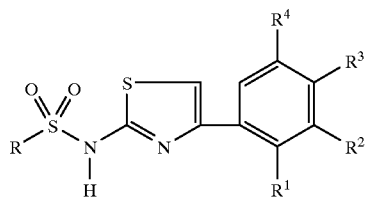

I wherein
R is lower-alkyl, phenyl, benzyl, naphthyl, pyridyl or thienyl, which are unsubstituted or substituted by one or more lower-alkyl, lower-alkoxy, lower-alkyl-carbonyl-amino, halogen, cycloalkyl, nitro, amino, methylenedioxy, phenoxy or benzyloxy substituents, and wherein the aromatic ring substituent, are unsubstituted or substituted by nitro, halogen or amino, $R^1$–$R^4$ are, independently, hydrogen, halogen, hydroxy, lower-alkyl, lower cycloalkyl, nitro, cyano, amino, lower-alkoxy, benzyloxy, trifluoromethyl or phenyl, which are unsubstituted or substituted by one or more lower-alkyl, trifluoromethyl, nitro, amino or hydroxy substituents, and wherein $R^1$ and $R^2$ or $R^2$ and $R^3$ together may form a benzene ring which is unsubstituted or substituted by halogen, trifluoromethyl, nitro, lower-alkyl or lower-alkoxy, or a pharmaceutically acceptable salt thereof.

2. A method according to claim 1, wherein R is 4-methylphenyl, 4-methoxyphenyl, 4-aminophenyl, 3,4-dimethoxyphenyl or 2-naphthyl.

3. A method according to claim 1, wherein $R^1$–$R^4$ are, independently, hydrogen, fluorine, nitro or trifluoromethyl, or $R^2$ and $R^3$ together form a benzene ring.

4. A method according to claim 1, wherein the compound of formula I is 4-methoxy-N-(4-naphthalen-2-yl-thiazol-2-yl)-benzene-sulfonamide.

5. A method according to claim 1, wherein the compound of formula I is 4-amino-N-[4-(3-nitro-phenyl)-thiazol-2-yl]-benzenesulfonamide.

6. A method according to claim 1, wherein the compound of formula I is 4-methyl-N-[4-(3-nitro-phenyl)-thiazol-2-yl]-benzenesulfonamide.

7. A method according to claim 1, wherein the compound of formula I is 3,4-dimethoxy-N-[4-(3-nitro-phenyl)-thiazol-2-yl]-benzenesulfonamide.

8. A method according to claim 1, wherein the compound of formula I is 4-methoxy-N-[4-(3-nitro-phenyl)-thiazol-2-yl]-benzenesulfonamide.

9. A method according to claim 1, wherein the compound of formula I is naphthalene-2-sulfonic acid [4-(3-nitro-phenyl)-thiazol-2-yl]-benzenesulfonamide.

10. A method according to claim 1, wherein the compound of formula I is N-[4-(2-fluoro-5-trifluoromethyl-phenyl)-thiazol-2-yl]-4-methyl-benzelesulfonamide.

11. A method according to claim 1, wherein the compound of formula I is N-[4-(3-fluoro-5-trifluoromethyl-phenyl)-thiazol-2-yl]-4-methyl-benzelesulfonamide.

12. A method according to claim 1, wherein the compound of formula I is 4-methyl-N-[4-(4-nitro-phenyl)-thiazol-2-yl]-benzenesulfonamide.

13. A method according to claim 1, wherein the compound of formula I is 4-amino-N-[4-(2-fluoro-5-trifluoromethyl-phenyl)-thiazol-2-yl]-benzenesulfonamide.

14. A method according to claim 1, wherein the compound of formula I is 3,4-dimethoxy-N-[4-(2-fluoro-5-trifluoromethyl-phenyl)-thiazol-2-yl]-benzenesulfonamide.

* * * * *